Figure 1:
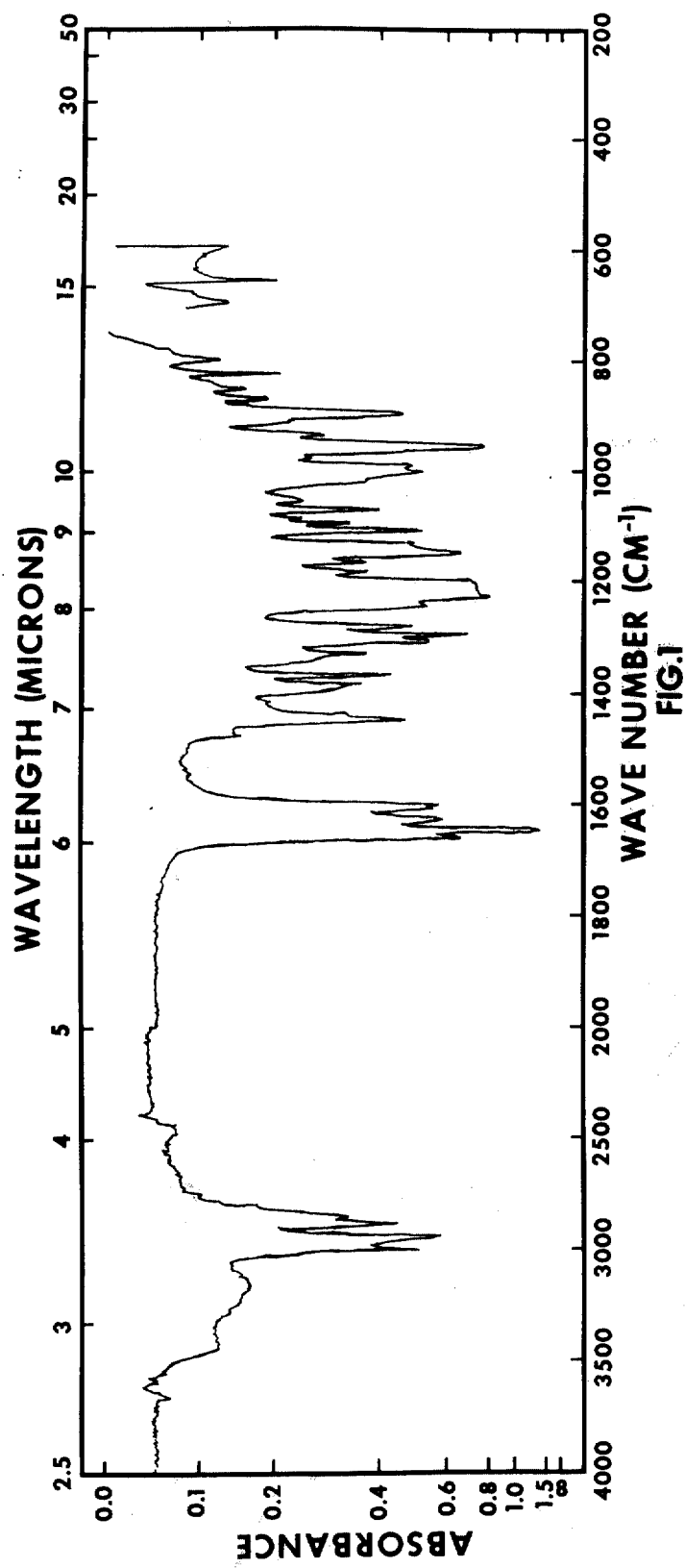

United States Patent [19]

Kluepfel et al.

[11] 4,003,902
[45] Jan. 18, 1977

[54] NAPHTHYRIDINOMYCIN ANTIBIOTICS

[75] Inventors: Dieter Kluepfel, Montreal; Surendra N. Sehgal, Dollard-des-Ormeaux; Claude Vezina, Oka, all of Canada

[73] Assignee: Ayerst McKenna and Harrison Ltd., Montreal, Canada

[22] Filed: June 20, 1974

[21] Appl. No.: 481,291

[52] U.S. Cl. .......................... 260/268 PC; 195/81
[51] Int. Cl.² .................................. C07D 498/22
[58] Field of Search ........................... 260/268 PC

[56] References Cited
UNITED STATES PATENTS
3,849,419  11/1974  Delong ............... 260/268 PC Primary Examiner—Richard J. Gallagher
Assistant Examiner—James H. Turnipseed

[57] ABSTRACT

Naphthyridinomycin complex, a major component thereof called naphthyridinomycin A and a minor component thereof called naphthyridinomycin B are disclosed. These antibiotic substances exhibit antibacterial activity. The substances are producible by culturing a microorganism of the species Streptomyces in an aqueous nutrient medium under submerged aerobic fermentation conditions. Methods for their preparation and use are included.

1 Claim, 3 Drawing Figures

NAPHTHYRIDINOMYCIN ANTIBIOTICS

BACKGROUND OF THE INVENTION

1. Field of Invention

The present invention relates to new antibiotic substances. More particularly, the invention relates to a microbial product called naphthyridinomycin complex, to individual components thereof called naphthyridinomycin A and naphthyridinomycin B, and to methods for the production of the foregoing substances.

2. Description of the Prior Art

Naphthyridinomycin complex as normally obtained from fermentation broths is a mixture comprising a major component (naphthyridinomycin A) and a minor component (naphthyridinomycin B). The major and minor components have many chemical and physical properties in common. The molecular structure of naphthyridinomycin A has been established by X-ray crystallography. The structure features a substituted quinone ring fused to an unusual alkaloid structure possessing three tertiary amines, see below. This unusual structure for naphthyridinomycin A appears to render this component, as well as the other antibiotic substance of this invention, unique in the field of antibiotics.

SUMMARY OF THE INVENTION

The antibiotic substances of this invention are obtained by culturing a naphthyridinomycin-producing organism in an aqueous nutrient medium under submerged aerobic fermentation conditions.

The naphthyridinomycin complex-producing organism, Streptomyces sp. NRRL 8034, was isolated from Easter Island soils and samples thereof have been deposited without restrictions with the Northeren Utilization and Research Division, Agricultural Research Service, U.S. Department of Agriculture, Peoria, Illinois, U.S.A.

It is to be understood that the invention is not limited to the use of the particular organism herein described, but includes variations and mutants obtained by natural selection or by treatment of the microorganism with, for instance, ultraviolet rays, X-rays, N-methyl-N'-nitro-N-nitrosoguanidine, manganese chloride, camphor, nitrogen mustards, and the like, as well as polyploids of the various mutants.

Streptomyces sp. NRRL 8034 develops abundantly in culture media usually employed for cultivation of other organisms of the same genus. It is capable of growing at temperatures ranging from 20° to 30° C, preferably at about 25° to 28° C, on Czapek's agar, oatmeal agar, nutrient agar, potato agar, glucose asparagine agar, glycerol asparagine agar, starch agar and peptone beef agar. Also, the organism grows very well on yeast extract agar, malt extract agar, starch-inorganic salts agar, oatmeal agar, tomato paste agar and Bennet's agar. Preferred media are tryptone-yeast extract agar (International Streptomyces Project (ISP) medium No. 1), yeast extract-malt extact agar (ISP No. 2), oatmeal agar (ISP No. 3), inorganic salts-starch agar (ISP No. 4), glycerol-asparagine agar (ISP No. 5), and tomato paste-oatmeal agar.

On yeast extract-malt extract agar (ISP No. 2) and tomato paste-oatmeal agar the aerial growth is gray with tiny white spots developing later during incubation at 25° C. On inorganic salts-starch agar (ISP No. 4), the grey color is lighter with small white spots. On oatmeal agar (ISP No. 3) and glycerolasparagine agar (ISP No. 5), it is grayish white.

Sporophores are rather loose, forming open loops (Retinaculi-Aperti) or open spirals (Spirae). Substrate growth is gray to whitish depending on the medium: grey on yeast extract-malt extract agar (ISP NO. 2), whitish on oatmeal agar (ISP No. 3), inorganic salts-starch agar (ISP No. 4), and glycerol-asparagine agar (ISP No. 5). It is brown on tomato paste-oatmeal agar. Spores are smooth. No soluble pigment is present on any medium. The organism is $H_2S$-negative (pertone-yeast extract iron agar, ISP No. 6) and melanine-negative (tyrosine agar, ISP No. 7).

Carbohydrate utilization by Streptomyces sp. NRRL 8034 was studied in carbon utilization agar (ISP No. 9) according to the procedure standardized by the International Streptomyces Project. The following carbohydrates were well utilized: D-glucose, L-arabinose, sucrose, D-xylose, inositol, D-mannitol, D-fructose, rhamnose, and starch. Carbohydrates not utilized were: raffinose and cellulose.

From the foregoing description and from the keys of classification published by Nomomura, J. Fermentation Technology, 52: 78–92 (1974), the naphthyridinomycin-producing organism Streptomyces sp. NRRL 8034 appears to belong to the species Streptomyces lusitanus.

The environmental and nutritional requirements for the fermentation of Streptomyces sp. NRRL 8034 are similar to those necessary for the production of antibiotics by other aerobic microorganisms. Thus, aerobiosis is sustained in a liquid nutrient medium inoculated with culture incubated in flasks placed on shaking machines. For industrial production, metal tanks with internal aeration and agitation by means of paddles can be susbstituted. The microoganism requires as nutrient elements assimilable carbon and organic nitrogenous substances. The presence of mineral salts is desirable. Cultivation is best effected when the initial pH of the culture medium is between 5.5 and 7.5, the optimum pH being around 5.8 to 6.5.

The utilizable sources of assimilable carbon for the production of the antibiotic substances are very diverse, there being included sugars (for example, glucose, fructose, mannitol, maltose, arabinose, rhamnose, xylose, and the like, dextrin, starches of different types of origin, glycerol, inositol and other polyalcohols, and animal and vegetable fats, as well as esters thereof. The sources of organic assimilable nitrogen which actively stimulate growth and favor production of the antibiotic substances of this invention are substances such as soybean meal, cotton seed meal and other vegetable meals (whole or partially or totally defatted), meat flours or animal viscera, various peptones, casein hydrolysates, soybean hydrolysates, yeast hydrolysates, lactalbumin, wheat glutens, distillers solubles, corn steeps, molasses, urea and amino acids.

Mineral salts, such as the chlorides, nitrates, sulfates, carbonates and phosphates of sodium, potassium, ammonium and calcium, should be included in appropriate concentrations. The nutritive medium should contain a number of trace elements such as magnesium, iron, manganese and zinc.

The fermentation medium is inoculated with a spore suspension of the organism obtained from a fresh slant culture of Streptomyces sp. NRRL 8034.

Under the described conditions and with the temperature of cultivation at about 20° – 35° C, preferably at about 25° – 28° C, substantial production of the desired antibiotic substances is obtained. Maximum production usually occurs within the period of about 72 to 120 hours.

Thereafter, a variety of procedures may be employed in the isolation and purification of the antibiotic substances, for example, solvent extraction, partition chromatography, chromatography on a varity of absorbents, liquid-liquid distribution in a counter current apparatus, and crystallization from solvents, The naphthyridinomycin complex of this invention is harvested conveniently by the following procedure:

a. adjusting the pH of the fermentation mixture to between pH 3 and pH 5, preferably pH 4.0, with an acid, preferably hydrochloric acid, sulfuric acid or phosphoric acid;

b. separating the mycelium from the fermentation mixture;

c. neutralizing the mycelium-free fermentation mixture by the addition of a base, preferably ammonium hydroxide, sodium hydroxide or potassium hydroxide;

d. treating the mixture with an absorbent, preferably a cation exchange resin, preferably one of the Amberlite IRC-50 type;

e. extracting the resulting cake of the absorbent with an acid solution, preferably, hydrochloric acid in methanol (0.1 to 1N) or aqueous hydrochloric acid (0.1 to 1N), to obtain an extract; and f. isolating the naphthyridinomycin complex from the extract.

Thereafter, and if desired, the naphthyridinomycin complex is separated into various components by known separation techniques. Partition or absorption chromatography are convenient and efficient techniques for this purpose.

DETAILS OF THE INVENTION

For the purpose of this disclosure the term "naphthyridinomycin complex" is used to describe the total antibiotically active material isolable from the fermentation broth by the process of this invention. The term "component" is used herein to describe a factor which is separated or isolated from the complex by known separation techniques. For convenience, individual components are arbitrarily designated naphthyridinomycin A and naphthyridinomycin B. The term "antibiotic substances" is used herein to describe collectively the naphthyridinomycin complex and the components.

The antibiotic substances of this invention have useful antimicrobial activity. For example, they are useful against a broad spectrum of pathogenic bacteria.

The antibacterial activity of the antibiotic substances of this invention is demonstrated in standard tests used for this purpose, for example, in the tests described in "Antiseptics, Disinfectants, Fungicides and Sterilization", G. F. Reddish, Ed., 2nd ed., Lea and Febiger, Philadelphia, 1957 or by D. C. Grove and W. A. Randall in "Assay Methods of Antibiotics", Med. Encycl. Inc., New York 1955.

For example, by employing a test like the serial broth dilution, see Reddish, cited above, in which dilutions of the antibiotic substances of this invention in nutrient broth are inoculated with the microorganisms, incubated at 37° C for one day, respectively, and examined for the presence of growth, it was shown that the antibiotic substances inhibit growth totally of a variety of pathogenic microorganisms. The results of such an experiment are reported hereinafter.

When the antibiotic of this invention are employed as antibacterial agents, they are used alone or in combination with pharmaceutically acceptable carriers, the proportion of which is determined by the solubility and chemical nature of the antibiotic substance, chosen route of administration and standard biological practice.

The dosage of the antibiotic substances will vary with the form of administration and the particular substance chosen. Furthermore, it will vary with the particular host under treatment. Generally, treatment is initiated with small dosages substantially less than the optimum dose of the substance. Thereafter, the dosage is increased by small increments until the optimum effect under the circumstances is reached. In general, the antibiotic substances of this invention are most desirably administered topically to pathogenic bacteria-infected skin of warm blooded animals at a concentration level that will generally afford antibacterially effective results without causing any harmful or deleterious side effects.

For topical application they are formulated in the form of solutions, creams or lotions in pharmaceutically acceptable vehicles containing 0.1 – 5 percent, preferably 0.5 to 2 percent, of the antibiotic substances and are administered topically to the infected area of the skin.

PREPARATION

In a preferred embodiment of this invention the antibiotic substances are obtained in the following manner:

A suitable fermenter is charged with a production medium (see Example 1). After sterilization and cooling, the medium is inoculated with a first stage inoculum preparation of *Streptomyces sp. NRRL* 8034.

The fermentation is allowed to proceed at 20° to 35° C, preferably 25° to 28° C. During the course of the fermentation the pH of the fermentation mixture is kept between 5.5 to 7.5, preferably 5.8 to 6.5 by the addition of a base, for example, 25% sodium, potassium or preferably ammonium hydroxide solution.

After about 72 to 120 hours, usually 96 hours, a maximum titre of the antibiotic substances of this invention is usually obtained. The concentration of the antibiotic substances in the fermentation mixture is readily followed during the course of the fermentation by testing samples of the mixture for their inhibitory effect of a strain of *Pseudomonas aeruginosa* or *Sarcina lutea* as determined by the cup plate method.

Thereafter the fermentation is stopped, and the pH of the mixture adjusted to about 4 with an acid, for example, sulfuric or hydrochloric acid. The mycelium is separated from the fermentation mixture by subjecting the mixture to filtration through a filter aid, for example, diatomaceous earth. The filtrate, i.e. the mycelium-free fermentation mixture, is adjusted to about pH 6.0 to 7.5, preferably 7.0, by the addition of base, for example, 1 N ammonium hydroxide or sodium hydroxide solution. The adjusted filtrate is now subjected to chromatography on a cation exchange resin, for example, Amberlite IRC-50, Dowex 30 or Wofatit C. Preferably Amberlite IRC-50 in the hydrogen cycle is used in an amount equal in volume to 1/10 to 1/30 the volume of the filtrate. Accordingly, the filtrate is passed through the exchange resin whereby the antibiotic substances are absorbed on the resin. The resin is then washed with distilled water and methanol. Thereafter the antibiotic substances are eluted with an acidic solution, preferably hydrogen chloride in methanol (0.1 to 1.0 N, preferably 0.1 N). The eluant is concentrated to about 1/60 or 1/75 its original volume. The concentrate is filtered. The filtrate is diluted with about five to ten times its volume of a miscible polar solvent, for example, methanol, acetone or preferably methylene chloride. After drying the solution is concentrated to about 1/100 to 1/50 its original volume. A non-polar solvent, preferably hexane or petroleum ether, is added to the latter concentrate. In this manner naphthyridomycin complex is obtained as a precipitate.

Naphthyridinomycin complex is separated into a major component (naphthyridomycin A) and a minor component (naphthyridinomycin B) in the following manner.

Naphthyridinomycin complex is subjected to chromatography on alumina. Naphthyridinomycin A, the least polar component, is eluted first. Concentration of the eluate affords naphthyridinomycin A as a crystalline solid. Increasing the polarity of the eluate gives a second antibiotic fraction which is crude naphthyridinomycin B. This latter substance is purified further by chromatography on alumina or preferably an anion exchange resin, for example, Sephadex DEAE 52, Amberlite IR-48 or Amberlite IR-45.

CHARACTERIZATION OF NAPHTHYRIDINOMYCIN COMPLEX a. Thin layer chromatography of naphthyridinomycin complex shows that it has a major component called naphthyridinomycin A and a minor component, called naphthyridinomycin B. The major component has an Rf of about 0.66 and the minor component has an Rf of about 0.50 on a thin layer plate of silica gel when using acetone-n-propanol-ethylene dichloride (6:2:3) as the mobile phase, and the major component has an Rf of about 0.78 and the minor component has an Rf of about 0.66 on a thin layer plate of alumina when using benzene-acetone-methanol (7:1.5:1.5) as the mobile phase.

Figure 2:
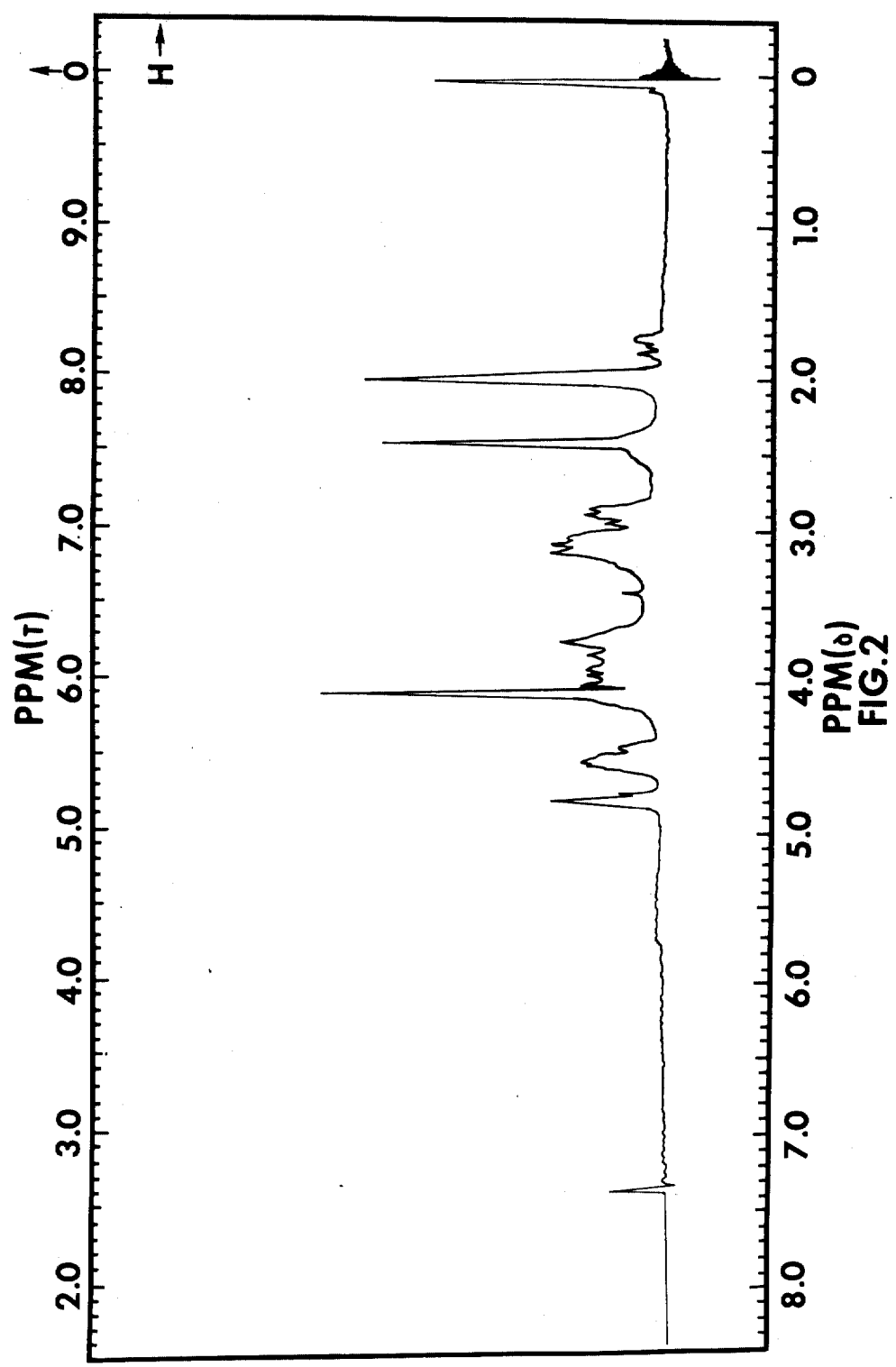

CHARACTERIZATION OF NAPHTHYRIDINOMYCIN A a. Naphthyridinomycin A is a compound having the formula:

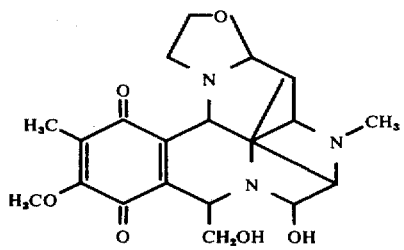

b. it is a ruby red crystalline compound having m.p. 108° – 110° C (dec.) after crystallization from dry ethyl ether.

c. It has a molecular formula of $C_{21}H_{27}N_3O_6$.

d. Naphthyridinomycin A has carbon, hydrogen and nitrogen in substantially the following proportions by weight:

|   | Percent (%) |
|---|---|
| C | 60.29 |
| H | 6.63 |
| N | 9.93 | as determined by microanalysis; the calculated C, H and N proportions for $C_{21}H_{27}N_3O_6$ is C, 60.42%; H, 6.52%; N, 10.07%.

e. It exhibits the following characteristic absorption maximum in its ultraviolet absorption spectrum: $\lambda_{max}$ 270 nm, $E_{1cm}^{1\%}$ 248.5 (MeOH).

f. Naphthyridinomycin A has a specific rotation ($[\alpha]_D^{25}$) of + 69.4° ($c = 1$, $CHCl_3$).

g. It is soluble in water, methanol, acetone, chloroform, methylene chloride, ethyl acetate and ether; insoluble in hexane.

h. The infrared absorption spectrum of naphthyridinomycin A is shown in accompanying FIG. 1; the spectrum shows characteristic absorption bands at 3000, 2940, 2880, 2845, 1715, 1690, 1650, 1604 and 1495 cm$^{-1}$.

i. The nuclear magnetic resonance spectrum of naphthyridinomycin A is shown in accompanying FIG. 2.

j. It has an Rf of about 0.66 on a thin layer plate of silica gel when using acetone-n-propanol-ethylene dichloride (6:2:3) as the mobile phase, and an Rf of about 0.78 on a thin layer plate of alumina when using benzene-acetone-methanol (7:1.5:1.5) as the mobile phase.

k. The minimum inhibitory concentration (MIC) of naphthyridinomycin A against various microorganisms is listed in Table 1.

l. Naphthyridinomycin A inhibits RNA and protein synthesis when tested according to the procedure of N. H. Munroe and A. Fleck, Analyst, 91, 78 (1966).

Figure 3:
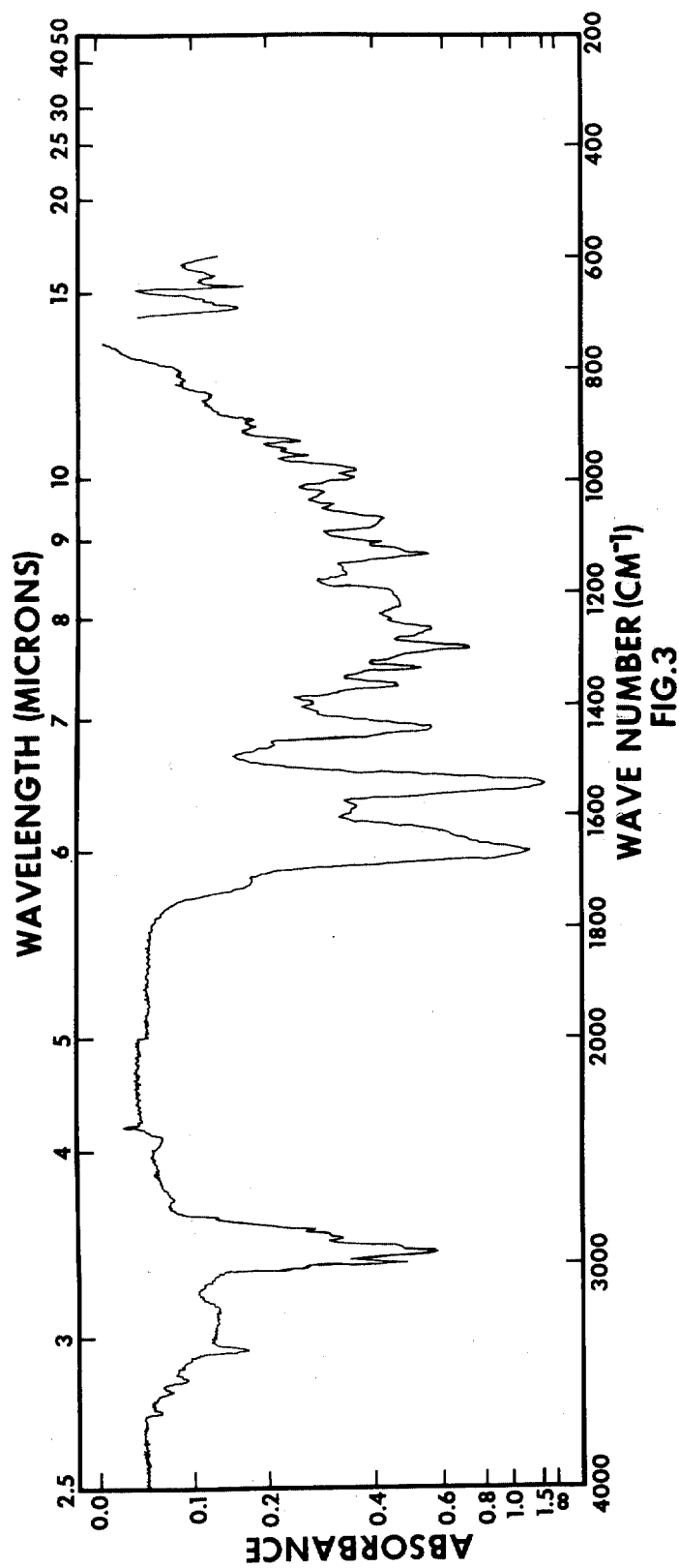

CHARACTERIZATION OF NAPHTHYRIDOMYCIN B a. Naphthyridinomycin B exhibits a characteristic absorption maximum in its ultraviolet absorption spectrum at 282 nm in methanol solution.

b. The infrared spectrum of naphthyridinomycin B is shown in accompanying FIG 3; the spectrum shows characteristic absorption bands at 3382, 2998, 2942, 1664, 1542, 1440, 1368, 1360, 1334, 1296 and 1132 cm$^{-1}$;

c. It has an Rf of about 0.50 on a thin layer plate of silica gel when using acetone-n-propanol-ethylene dichloride (6:2:3) as the mobile phase, and a Rf of about 0.66 on a thin layer plate of alumina when using benzene-acetone-methanol (7:1.5:1.5) as the mobile phase.

d. The MIC of naphthyridinomycin B against the various microorganisms is listed in Table 1.

TABLE 1

Minimum Inhibitory Concentration (MIC) in mcg/ml for Naphthyridinomycin A and Naphthyridinomycin B

| Test Microorganism | Naphthyridinomycin A | Naphthyridinomycin B |
|---|---|---|
| Staphylococcus pyogenes (penicillin-sensitive) | <0.025 | 0.2 |
| Staphylococcus pyogenes | | |

TABLE 1-continued

Minimum Inhibitory Concentration (MIC) in mcg/ml for Naphthyridinomycin A and Naphthyridinomycin B

| Test Microorganism | Naphthyridinomycin A | Naphthyridinomycin B |
| --- | --- | --- |
| (penicillin-resistant) | <0.025 | 0.2 |
| Streptococcus faecalis | <0.025 | 1.6 |
| Escherichia coli | 0.8 | 25 |
| Aerobacter aerogenes | 0.2 | 3.125 |
| Salmonella pullorum | 0.2 | 6.25 |
| Pseudomonas aeruginose | 0.2 | 25 |
| Pseudomonas fluorescens | 1.6 | 50 |
| Proteus mirabilis | 0.4 | 25 |
| Proteus vulgaris | 0.4 | 25 |
| Klebsiella pneumoniae | 0.05 | 1.6 |
| Serratia marcescens | 0.05 | 6.25 |

The following examples illustrate further this invention.

EXAMPLE 1

Preparation of Naphthyridinomycin Complex

Microorganism

*Streptomyces sp.* NRRL 8034 was grown and maintained on oatmeal or tomato paste agar slants (T. G. Pridham, et al., Antibiotic Annual 1956 – 1957, Medical Encyclopedia Inc., New York, p. 947) and in Roux bottles containing the same medium. Good growth was obtained after 7 days of incubation at 28° C. Spores from one Roux bottle were washed off and suspended into 50 ml of sterile distilled water. This suspension was used to inoculate the first stage inoculum.

First Stage Inoculum

The first stage inoculum medium is an aqueous medium having the following constituents:

| | |
| --- | --- |
| glucose ("Cerelose", Corn Products Corp., New York, N.Y.) | 2.0% |
| peptone ("Bacto-Neopeptone", Difco Labs, Detroit, Mich.) | 0.8% |
| tomato paste | 1.0% |
| corn meal | 0.8% |
| "Blackstrap" molasses | 2.0% |
| sodium chloride | 0.3% |

The above medium was sterilized in an autoclave at 121° C for 20 minutes, cooled and adjusted to pH 7.8 with ammonium hydroxide.

The first stage inoculum medium (3.2 l), contained in a 24 liter Florence flask, was sterilized at 121° C for 20 minutes, cooled and inoculated with 32 ml (1% inoculum) of the spore suspension described above. The inoculated flask was incubated for 18 – 24 hours at 28° C on a reciprocating shaker operating at 65 rev/min 4 in. stroke).

Production stage

The production stage was run in 250 liter New Brunswick fermenters, Model F-250, equipped with automatic antifoam addition system and pH recorder-controller. The fermenters were charged with 160 liters of the same medium described above and lard oil (0.1% v/v, Larex No. 1, Swift Canadian Co., Toronto) was added as an antifoam agent before sterilization. The fermenters were sterilized at 121° C for 30 minutes. The sterilized and cooled fermenters were inoculated with one flask (3.2 l, 2% inoculum) of first stage inoculum. Incubation temperature: 28° C; aeration: 0.5 vol/-vol/min; agitation: 250 rev/min. The antifoam agent, used on demand, was Mazu DF-143PX (Mazer Chemical, Inc., Gurnee, Illinois). During the course of fermentation pH was kept at 6.0 by automatic addition of 25% sodium hydroxide solution.

After 96 hours of incubation, a 1.3 cm diameter filter paper disc in broth gave an inhibition zone of 8 mm on an agar plate seeded with a strain of *Pseudomonas aeruginosa*. At this time the packed cell volume (PCV) was 24 to 28%. The fermentation was stopped, the pH of the broth was adjusted to 4.0 with conc. HCl, and diatomaceous earth (5% v/v) was added. The mixture was subjected to filtration. The filtrate containing the antibiotic principle was retained and the mycelium discarded.

Extraction and Recovery

The pH of the filtrate (volume = 150 liters) was adjusted to 7.0 with 1N ammonium hydroxide solution. The filtrate was passed through a column containing 7 liters of Amberlite IRC 50 $H^+$ resin at a rate of 10 liters per hour. The product was absorbed on the resin and the eluate was rejected. The resin was washed with deionized water until the washings were colorless; followed by a wash with methanol to displace water from the column. The product was eluted from the resin with 12 to 15 liters of 0.2 N HCl in methanol. The eluate was decolorized with 1% activated charcoal (Darco G-60) and concentrated under reduced pressure at about 40° C to about 200 ml. The concentrate was filtered. The filtrate was mixed with about 2000 ml of methylene chloride and the upper aqueous layer discarded. The methylene chloride solution was dried ($Na_2SO_4$) and concentrated to 30 – 50 ml under reduced pressure. Addition of hexane to the concentrate precipitated naphthyridinomycin complex as a yellow solid, which was dried thoroughly under reduced pressure.

EXAMPLE 2

Separation of Naphthyridinomycin Complex into a Major and Minor Component

Naphthyridinomycin complex, obtained as described in Example 1, was subjected to chromatography on aluminum oxide (activity V, Woelm, Germany). The charge-absorbant ratio was 1:100. Benzene-chloroform (80:20) was used as the eluant.

The fractions were collected and analyzed by TLC. The antibiotic-containing fractions were pooled and evaporated to a small volume under reduced pressure. The product crystallized spontaneously along the wall of the vessel. The compound was recrystallized from dry ethyl ether and dried thoroughly under reduced pressure to give naphthyridomycin A.

Upon increasing the percentage of chloroform in the above eluant to 30%, another antibiotic substance was obtained by hexane precipitation of the ensuing antibiotic fractions.

This latter antibiotic substance was purified further by passing it through a column of the cellulose-based anion exchanger, Sephadex DEAE 52, in aqueous solution. The active fractions were collected and the water evaporated under reduced pressure. The residue was dissolved in a minimum volume of chloroform. Addition of hexane to the latter solution precipitated naphthyridinomycin B as a solid which was dried under reduced pressure.

We claim:
1. Naphthyridinomycin A, which
   a. is a ruby red crystalline compound having mp 108° – 110° C (dec) after crystallization from dry ethyl ether;
   b. has a molecular formula of $C_{21}H_{27}N_3O_6$;
   c. has C, H and N in substantially the following proportions by weight; C, 60.29%; H, 6.63%; and N, 9.93%;
   d. exhibits a characteristic absorption maximum in its ultraviolet absorption spectrum of $\lambda_{max}$ 270 nm, $E_{1cm}^{1\%}$ 248.5 (MeOH);
   e. has a specific rotation $[\alpha]_D^{25}$ of + 69.4° ($c = 1$, $CHCl_3$);
   f. is soluble in water methanol, acetone, chloroform, methylene chloride, ethyl acetate and ether; insoluble in hexane;
   g. has an infrared spectrum as shown in accompanying FIG. 1;
   h. has nuclear magnetic resonance spectrum as shown in accompanying FIG. 2;
   i. has an Rf of about 0.66 on a thin layer plate of silica gel when using acetone-n-propanol-ethylene dichloride (6:2:3) as the mobile phase;
   j. has an Rf of about 0.78 on a thin layer plate of alumina when using benzene-acetone-methanol (7:1.5:1.5) as the mobile phase; and
   k. has the structural formula

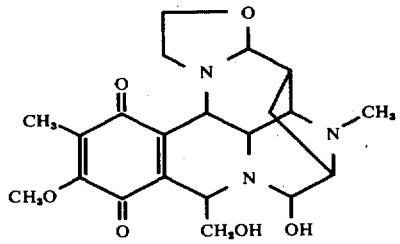

* * * * *